US012595498B2

(12) United States Patent
Murase

(10) Patent No.: US 12,595,498 B2
(45) Date of Patent: Apr. 7, 2026

(54) METHOD FOR PRODUCING CELLOOLIGOSACCHARIDE

(71) Applicant: DKS Co. Ltd., Kyoto (JP)

(72) Inventor: Rina Murase, Kyoto (JP)

(73) Assignee: DKS CO. LTD., Kyoto (JP)

( * ) Notice: Subject to any disclaimer, the term of this patent is extended or adjusted under 35 U.S.C. 154(b) by 386 days.

(21) Appl. No.: 18/270,750

(22) PCT Filed: Dec. 15, 2021

(86) PCT No.: PCT/JP2021/046312
§ 371 (c)(1),
(2) Date: Jul. 3, 2023

(87) PCT Pub. No.: WO2022/153771
PCT Pub. Date: Jul. 21, 2022

(65) Prior Publication Data

US 2024/0336944 A1 Oct. 10, 2024

(30) Foreign Application Priority Data

Jan. 12, 2021 (JP) ................................ 2021-003076

(51) Int. Cl.
*C12P 19/04* (2006.01)
*C12N 9/10* (2006.01)

(52) U.S. Cl.
CPC ............ *C12P 19/04* (2013.01); *C12N 9/1051* (2013.01); *C12Y 204/01007* (2013.01); *C12Y 204/01049* (2013.01)

(58) Field of Classification Search
CPC ........ C12P 19/04; C12P 19/00; C12N 9/1051; C12Y 204/01007; C12Y 204/01049
See application file for complete search history.

(56) References Cited

U.S. PATENT DOCUMENTS

| | | | | |
|---|---|---|---|---|
| 7,968,309 | B2 * | 6/2011 | Fujii | C12N 9/1051 435/100 |
| 11,505,813 | B2 * | 11/2022 | Serizawa | C12P 19/18 |
| 2007/0092949 | A1 * | 4/2007 | Odan | C12P 19/04 536/123.12 |
| 2021/0238641 | A1 | 8/2021 | Serizawa et al. | |

FOREIGN PATENT DOCUMENTS

JP 2019-193601 A 11/2019

OTHER PUBLICATIONS

Griessler et al., Optimization of Glucose-1-Phosphate Production Employing Glucan-Phosphorylases in Continuous Enzyme Membrane Reactors. Annals NY Academy Sci., 1996, pp. 494-500. (Year: 1996).*
Kitaoka et al., Diversity of phosphorylases in glycoside hydrolase families. Appl Microbiol Biotechnol., 2015, vol. 99: 8377-8390. (Year: 2015).*
Petrovic et al., Characterization of oligocellulose synthesized by reverse phosphorolysis using different cellodextrin phosphorylases. Anal Chem., 2015, vol. 87: 9639-9646. (Year: 2015).*
International Search Report for International Application No. PCT/JP2021/046312, dated Mar. 1, 2022.
Sakai, "New oligosaccharides and functionality," The Food Industry, vol. 46, No. 6, 2003, pp. 43-52.
Written Opinion of the International Searching Authority for International Application No. PCT/JP2021/046312, dated Mar. 1, 2022.

* cited by examiner

*Primary Examiner* — Ganapathirama Raghu
(74) *Attorney, Agent, or Firm* — Birch, Stewart, Kolasch & Birch, LLP

(57) ABSTRACT

A method by which a cellooligosaccharide can be produced inexpensively at high percentage yield is provided. In the method for producing a cellooligosaccharide according to an embodiment, at least one primer selected from the group consisting of glucose, cellobiose, and derivatives in which anomeric positions of glucose and cellobiose are modified and sucrose are subjected to, in the presence of phosphoric acid, actions of sucrose phosphorylase and cellodextrin phosphorylase. In this case, in the reaction system, the concentration of phosphoric acid is set to 3 mol/$m^3$ or more and 120 mol/$m^3$ or less.

6 Claims, No Drawings

METHOD FOR PRODUCING CELLOOLIGOSACCHARIDE

TECHNICAL FIELD

The present invention relates to a method for producing a cellooligosaccharide using enzymes.

BACKGROUND ART

As a method for producing, using an enzyme, a cellulose oligomer, namely, a cellooligosaccharide, there is a known synthesis method using the reverse reaction of a phosphorylase that is cellodextrin phosphorylase (CDP).

For example, Patent Literature 1 states that primers such as α-glucose-1-phosphate and glucose are caused to react in a mixed solvent containing water and a water-soluble organic solvent by the action of cellodextrin phosphorylase to synthesize a cellooligosaccharide.

CITATION LIST

Patent Literature

PTL 1: Japanese Unexamined Patent Application Publication No. 2019-193601

SUMMARY OF INVENTION

Technical Problem

However, in the above-described synthesis method, α-glucose-1-phosphate serving as a starting material is very expensive and the cellooligosaccharide is not necessarily provided at high percentage yield, which have been problematic.

Under such circumstances, an object of an embodiment of the present invention is to provide a method by which a cellooligosaccharide can be produced inexpensively at high percentage yield.

Solution to Problem

A method for producing a cellooligosaccharide according to an embodiment of the present invention is a method for producing a cellooligosaccharide, the method including a reaction step of subjecting at least one primer selected from the group consisting of glucose, cellobiose, and derivatives in which anomeric positions of glucose and cellobiose are modified and sucrose, to, in the presence of phosphoric acid, actions of sucrose phosphorylase and cellodextrin phosphorylase, wherein, in a reaction system, a concentration of phosphoric acid including an amount of α-glucose-1-phosphate contained as an intermediate product is 3 $mol/m^3$ or more and 120 $mol/m^3$ or less.

Advantageous Effects of Invention

In an embodiment according to the present invention, sucrose phosphorylase is used to generate, from sucrose, α-glucose-1-phosphate, and, from the obtained α-glucose-1-phosphate and the primer, cellodextrin phosphorylase is used to generate a cellooligosaccharide, so that the cellooligosaccharide can be produced inexpensively. In addition, the concentration of phosphoric acid in the reaction system is specified, so that the percentage yield of the cellooligosaccharide can be increased.

DESCRIPTION OF EMBODIMENTS

In a method for producing a cellooligosaccharide according to this embodiment, at least one selected from the group consisting of glucose, cellobiose, and derivatives in which anomeric positions of glucose and cellobiose are modified is used as a primer; sucrose and the primer are subjected to, in the presence of phosphoric acid, actions of sucrose phosphorylase (hereafter, also referred to as SP) and cellodextrin phosphorylase (hereafter, also referred to as CDP).

This reaction is, as represented by the following formula, a combination of a reaction of using SP to generate, from sucrose and phosphoric acid, α-glucose-1-phosphate (hereafter, also referred to as αG1P) and a reaction of using CDP to generate, from αG1P and the primer, a cellooligosaccharide; with sucrose serving as a glucose donor and the primer serving as a glucose acceptor, actions of the two phosphorylases are used to synthesize the cellooligosaccharide in two stages.

[Chem. 1]

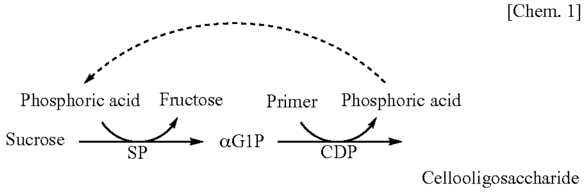

The first-stage reaction is a reaction of using the sucrose phosphorylase SP to generate αG1P in which sucrose, which is inexpensive, is used as the starting material to synthesize αG1P. The second-stage reaction uses the reverse reaction of the phosphorylase CDP in which, to the primer serving as a glucose acceptor, αG1P serving as a monomer is polymerized in stepwise manner, to provide a cellooligosaccharide having a cellulose II crystalline structure. This two-stage synthesis enables single-batch synthesis of the cellooligosaccharide from sucrose, which is inexpensive. In addition, phosphoric acid generated in the reaction caused by CDP is consumed in the reaction caused by SP; in other words, phosphoric acid is circulated within the reaction system, so that phosphorolysis caused by accumulation of phosphoric acid can be suppressed to achieve an increase in the percentage yield of the cellooligosaccharide.

The sucrose serving as the glucose donor is not particularly limited and may be a naturally occurring sucrose or a chemically synthesized sucrose. The sucrose initial concentration (in other words, the concentration at the time of charging; hereafter, the same definition) in the reaction system (ordinarily, a reaction solution; hereafter, the same definition) is not particularly limited and may be, for example, 10 to 1000 $mol/m^3$ or may be 100 to 500 $mol/m^3$.

The primer serving as the glucose acceptor is, as described above, at least one selected from the group consisting of glucose, cellobiose, and derivatives in which anomeric positions of glucose and cellobiose are modified. Such a derivative has, at the anomeric position of glucose or cellobiose, a substituent and is more specifically a derivative in which a hydroxy group bonded to the carbon atom at the anomeric position is substituted with another organic group (substituent). Examples of the substituent include alkoxy groups, organic groups including an azide group (also including organic groups in which the azide group is directly bonded to the carbon atom at the anomeric position), and organic groups including an amino group (also including organic groups in which the amino group is directly bonded to the carbon atom at the anomeric position). The amino group may be a primary amino group, may be a secondary amino group, or may be a tertiary amino group.

The glucose derivative is, for example, represented by the following General formula (1).

[Chem. 2]

(1)

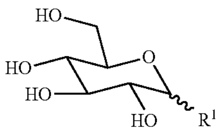

In Formula (1), $R^1$ preferably represents —$OR^2$, —$R^3$—$N_3$, or —$R^4$—$NH_2$. In the formula, the wavy line indicates that the configuration at the anomeric position is the α form, the β form, or a mixture of the α form and the β form.

$R^2$ preferably represents a hydrocarbon group having 1 to 12 carbon atoms. The hydrocarbon group may be an aliphatic hydrocarbon group or may be an aromatic hydrocarbon group, and is preferably an alkyl group that may have a linear chain or a branched chain. The number of carbon atoms of the hydrocarbon group is preferably 1 to 5, more preferably 1 to 3. $R^2$ preferably represents an alkyl group having 1 to 5 carbon atoms and more preferably represents an alkyl group having 1 to 3 carbon atoms.

In the case where $R^1$ is —$OR^2$, specific examples include alkyl glucosides such as methyl glucoside, ethyl glucoside, octyl glucoside, decyl glucoside, and dodecyl glucoside, and aryl glucosides such as phenyl glucoside.

$R^3$ represents a direct bond or —$OR^5$—. $R^5$ represents a divalent hydrocarbon group having 1 to 20 carbon atoms. The divalent hydrocarbon group may be a divalent aliphatic hydrocarbon group or may be a divalent aromatic hydrocarbon group. The divalent aliphatic hydrocarbon group is, for example, an alkanediyl group or alkenediyl group that may have a linear chain or a branched chain. The divalent aromatic hydrocarbon group is, for example, a divalent aliphatic hydrocarbon group having an aromatic ring substituent or an arene diyl group in which substituents such as alkyl groups may be added to the aromatic rings. The number of carbon atoms of $R^5$ is preferably 1 to 10, more preferably 1 to 5. $R^5$ is preferably an alkanediyl group having 1 to 10 carbon atoms, more preferably an alkanediyl group having 1 to 5 carbon atoms.

In the case where $R^1$ is —$R^3$—$N_3$, specific examples include azidodeoxy glucoside and azidoalkyl glucosides (for example, azidoethyl glucoside).

$R^4$ represents a direct bond or —$OR^6$—. $R^6$ represents a divalent hydrocarbon group having 1 to 20 carbon atoms. The divalent hydrocarbon group may be a divalent aliphatic hydrocarbon group or may be a divalent aromatic hydrocarbon group. The divalent aliphatic hydrocarbon group is, for example, an alkanediyl group or alkenediyl group that may have a linear chain or a branched chain. The divalent aromatic hydrocarbon group is, for example, a divalent aliphatic hydrocarbon group having an aromatic ring substituent or an arene diyl group in which substituents such as alkyl groups may be added to the aromatic rings. The number of carbon atoms of $R^6$ is preferably 1 to 10, more preferably 1 to 5. $R^6$ is preferably an alkanediyl group having 1 to 10 carbon atoms, more preferably an alkanediyl group having 1 to 5 carbon atoms.

In the case where $R^1$ is —$R^4$—$NH_2$, specific examples include aminodeoxy glucoside and aminoalkyl glucosides (for example, aminoethyl glucoside).

The cellobiose derivative is, for example, represented by the following General formula (2).

[Chem. 3]

(2)

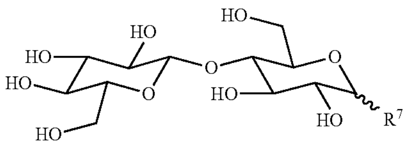

In Formula (2), $R^7$ is the same as $R^1$ in Formula (1); the wavy line indicates that the configuration at the anomeric position is the α form, the β form, or a mixture of the α form and the β form.

In an embodiment, the primer is preferably at least one selected from the group consisting of glucose and a glucose derivative in which the anomeric position of glucose is modified. In the case of using glucose or a derivative of glucose, compared with the case of using cellobiose, a cellooligosaccharide tends to precipitate (deposit) and is more easily purified, which is advantageous.

In the reaction system, the primer initial concentration is not particularly limited and may be, for example, 5 to 300 $mol/m^3$, may be 10 to 200 $mol/m^3$, or may be 30 to 100 $mol/m^3$. In the reaction system, the molar ratio (sucrose/primer ratio) of sucrose to the primer at the time of charging is also not particularly limited and may be, for example, 20/1 to 1/1, may be 15/1 to 4/3, or may be 10/1 to 2/1.

The phosphoric acid is used in the reaction of using SP to generate αG1P; due to the presence of phosphoric acid, from sucrose, αG1P and fructose are generated. The phosphoric acid is not particularly limited, may be an inorganic phosphoric acid, may be an inorganic phosphate such as sodium dihydrogen phosphate, potassium dihydrogen phosphate, disodium hydrogen phosphate, or dipotassium hydrogen phosphate, or may be one or in combination of two or more of the foregoing. As the phosphoric acid, a phosphate buffer solution may be used.

In this embodiment, the concentration of phosphoric acid in the reaction system is set to 3 to 120 $mol/m^3$. When the concentration of phosphoric acid is 3 $mol/m^3$ or more, the reaction of using SP to generate αG1P can be accelerated to increase the percentage yield of the cellooligosaccharide. When the concentration of phosphoric acid is 120 $mol/m^3$ or less, phosphorolysis caused by CDP can be suppressed to increase the percentage yield of the cellooligosaccharide. The concentration of phosphoric acid in the reaction system is preferably 7 to 80 $mol/m^3$, more preferably 8 to 70 $mol/m^3$.

The concentration of phosphoric acid in the reaction system is the concentration (molarity) of the entirety of phosphoric acid in the reaction system including the amount of α-glucose-1-phosphate contained as an intermediate product and is the total of the molarity of the inorganic phosphoric acid and/or inorganic phosphate and the molarity of αG1P. In order to provide such a concentration of phosphoric acid, for example, the phosphoric acid can be charged, as the inorganic phosphoric acid and/or inorganic phosphate, into the reaction system at an initial concentration of 3 to 120 mol/$m^3$, preferably 7 to 80 mol/$m^3$, more preferably 8 to 70 mol/$m^3$.

The sucrose phosphorylase (SP) is derived without particular limitations and may be, for example, derived from microorganisms such as *Leuconostoc mesenteroides* (*Leuconostoc mesenteroides*) or Streptococcusmutans (Streptococcusmutans).

The amount of SP used in the reaction system is not particularly limited, may be, for example, 0.001 to 10 U/mL, or may be 0.01 to 1 U/mL. The SP enzyme amount is determined on the basis of 1 U being defined as an enzyme amount in which, at 37° C. and at pH 7, from 100 mol/$m^3$ of sucrose and 50 mol/$m^3$ of phosphoric acid, 1 μmol of αG1P is released per minute.

The cellodextrin phosphorylase (CDP) is derived without particular limitations and may be, for example, derived from microorganisms such as *Clostridium thermocellum* (*Clostridium thermocellum*) or Cellulomonas (Cellulomonas). For example, for CDP, *Clostridium thermocellum* YM4-derived CDP can be prepared using an *E. coli* expression system in accordance with the method described in M. Krishnareddy et al., J. Appl. Glycosci., 2002, 49, 1-8.

In the reaction system, the amount of CDP used is not particularly limited, may be, for example, 0.01 to 10 U/mL, or may be 0.1 to 1 U/mL. The CDP enzyme amount is determined on the basis of 1 U being defined as an enzyme amount in which, in a 3-morpholinopropanesulfonic acid buffer solution (50 mM, pH: 7.5) containing 50 mol/$m^3$ of αG1P, 50 mol/$m^3$ of D-(+)-cellobiose, and CDP diluted the predetermined fold such that the αG1P conversion ratio for a reaction time of 100 minutes becomes 10% or less, incubated at 37° C., and quantified for the amount of phosphoric acid generated by CDP, 1 μmol of phosphoric acid is released per minute.

The enzymatic reaction using SP and CDP according to this embodiment is performed ordinarily in a reaction solution containing water as a solvent and is more specifically performed: a reaction solution prepared by mixing sucrose, the primer, phosphoric acid, SP, and CDP together with the solvent so as to provide the predetermined concentrations is held at the predetermined temperature and incubated.

The reaction temperature is preferably 25 to 45° C. When the reaction temperature is 25° C. or more, the enzymatic reaction rate can be increased. In the case of 45° C. or less, the decrease in the percentage yield of the cellooligosaccharide can be suppressed.

The reaction time is not particularly limited and may be, for example, 1 hour to 15 days or may be 1 day to 10 days.

The reaction solution preferably has a pH of about 5.0 to about 9.0. The pH of the reaction solution may be adjusted by, in addition to the phosphate buffer solution contributing to the reaction, adding, for example, tris(hydroxymethyl) aminomethane hydrochloride buffer solution, citric acid, 3-morpholinopropanesulfonic acid (MOPS), or hydroxyethyl piperazine ethanesulfonic acid (HEPES).

In an embodiment, as the solvent in the enzymatic reaction, a mixed solvent prepared by mixing together water and a water-soluble organic solvent may be used. Specifically, in a mixed solvent containing water and a water-soluble organic solvent, the primer and sucrose may be subjected to actions of SP and CDP. Use of such a mixed solvent can lower the distribution of degrees of polymerization of the cellooligosaccharide. Note that the mixed solution is prepared by, for example, mixing together a buffer solution being an aqueous solution and a water-soluble organic solvent.

The water-soluble organic solvent is an organic solvent having a solubility of 5 mL or more at 20° C. in 100 mL of water; examples include alcohols having 1 to 4 carbon atoms such as methanol, ethanol, 1-propanol, isopropyl alcohol, and t-butanol; ketones such as acetone; ethers such as tetrahydrofuran, amides such as N,N-dimethylformamide, N,N-dimethylacetamide, and N-methylpyrrolidone; nitriles such as acetonitrile; and sulfoxides such as dimethyl sulfoxide. These may be used alone or in combination of two or more thereof. More preferably, the water-soluble organic solvent is at least one selected from the group consisting of methanol (MeOH), ethanol (EtOH), N,N-dimethylformamide (DMF), and dimethyl sulfoxide (DMSO).

The buffer solution mixed with the water-soluble organic solvent is not particularly limited; examples include a HEPES buffer solution, a trishydrochloride buffer solution, a MOPS buffer solution, an acetate buffer solution, and a phosphate buffer solution; a buffer solution with which, at the reaction temperature, the reaction solvent is kept at a pH of about 5 to about 9 is preferably used.

The ratio between water and the water-soluble organic solvent used is not particularly limited; relative to 100 vol % of the mixed solvent, the water-soluble organic solvent preferably accounts for 5 to 50 vol %, more preferably 5 to 30 vol %, still more preferably 8 to 20 vol %.

After completion of the reaction, a reaction solution containing a cellooligosaccharide can be obtained. The reaction solution may contain enzymes that are SP and CDP, sucrose, the primer, and the like and hence, in order to remove these, may be rinsed. The rinsing can be performed by repeating a step of performing centrifugation to cause separation into precipitate and supernatant and using a rinsing solvent such as water to re-disperse the precipitate, to obtain a cellooligosaccharide.

The obtained cellooligosaccharide is an oligosaccharide having a structure in which glucoses are linked together via a β-1,4 glycoside bond. The degree of polymerization of the cellooligosaccharide may be, for example, 4 or more, 5 or more, or 6 or more, or may be, for example, 16 or less, 15 or less, or 13 or less. The average degree of polymerization (DP) is not particularly limited and may be, for example, 5.5 or more, 6.0 or more, 6.5 or more, or 7.0 or more. The average degree of polymerization (DP) may be, for example, 10.0 or less, 9.5 or less, or 9.0 or less.

The obtained cellooligosaccharide is, for example, represented by the following General formula (3).

[Chem. 4]

(3)

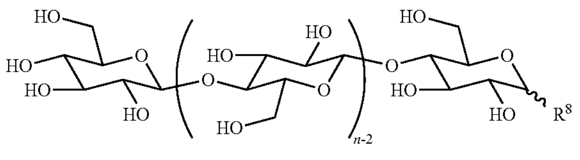

In Formula (3), $R^8$ preferably represents a hydroxy group, $R^1$, or $R^7$; n is an integer and indicates the degree of polymerization of the cellooligosaccharide. In the formula, the wavy line indicates that the configuration at the anomeric position is the α form, the β form, or a mixture of the α form and the β form.

In the case of using, as a primer, glucose or cellobiose, $R^8$ is a hydroxy group. In the case of using, as a primer, a glucose derivative represented by Formula (1) above, $R^8$ is $R^1$ in General formula (1) above. In the case of using, as a primer, a cellobiose derivative represented by Formula (2) above, $R^8$ is $R^7$ in General formula (2) above. In the case of using the glucose derivative or the cellobiose derivative as a primer, a reducing-terminal-modified cellooligosaccharide in which the anomeric position at the reducing terminal is modified is obtained. The cellooligosaccharide according to this embodiment also encompasses such cellooligosaccharide derivatives and also clearly encompasses alkali metal ion adducts such as sodium ion adducts and potassium ion adducts. Note that a cellooligosaccharide in which $R^8$ is an alkoxy group may be synthesized and subsequently hydrolyzed, to thereby produce a cellooligosaccharide in which $R^8$ is a hydroxy group.

The cellooligosaccharide according to this embodiment is applicable without particular limitations and is applicable to various publicly known applications such as the pharmaceutical field.

EXAMPLES

Hereinafter, the present invention will be described further with reference to Examples but is not limited to these. Note that, in EXAMPLES, "mol/m$^3$" and "mol/L" will be respectively described as "mM" and "M".

Reagents

In EXAMPLES, as water, ultrapure water provided by purification using a Milli-Q system (Milli-Q Advantage A-10, Merck Millipore) was used unless otherwise specified.

A 200 mM phosphate buffer solution used was prepared by adding, to a 0.2 M aqueous sodium dihydrogen phosphate solution, a 0.2 M disodium hydrogen phosphate solution so as to adjust the pH to 7.4. Note that the initial concentration of phosphoric acid in EXAMPLES is the total of the concentration of sodium dihydrogen phosphate and the concentration of disodium hydrogen phosphate.

A 1 M HEPES buffer solution used was prepared by dissolving 23.8 g of 2-[4-(2-hydroxyethyl)-1-piperazinyl] ethanesulfonic acid (HEPES) in 60 mL of water, adding, to the resultant aqueous solution, a 4 N aqueous sodium hydroxide solution to adjust the pH to 7.5, and subsequently adding water to a volume of 100 mL in a measuring flask.

A 20 mM MOPS buffer solution used was prepared by dissolving 4.18 g of 3-morpholinopropanesulfonic acid (MOPS) in 600 mL of water, adding, to the resultant aqueous solution, a 4 N aqueous sodium hydroxide solution to adjust the pH to 7.5, subsequently adding water to a volume of 1 L in a measuring flask, and further performing filter sterilization using a 0.22 μm filter made of PVDF.

A SP solution used was prepared by mixing together a sucrose phosphorylase (SP) powder (*Leuconostoc mesenteroides*-derived, manufactured by Oriental Yeast Co., Ltd.) and a 20 mM MOPS buffer solution (pH: 7.5) and performing adjustment to 10 U/mL of SP.

CDP was prepared in accordance with the method described in M. Krishnareddy et al., J. Appl. Glycosci., 2002, 49, 1-8. Specifically, CDP used was prepared in accordance with the method described in Paragraphs 0061 to 0070 of PTL 1 (Japanese Unexamined Patent Application Publication No. 2019-193601); the obtained CDP was mixed with a 20 mM MOPS buffer solution (pH: 7.5) and adjustment was performed to 10 U/mL of CDP.

ProteoMass™ Bradykinin fragment 1-7 MALDI-MS standard (Bradykinin), ProteoMass™ $P_{14}R$ MALDI-MS standard ($P_{14}R$), ProteoMass™ ACTH Fragment 18-39 MALDI-MS standard (ACTH), trifluoroacetic acid (TFA), and acetonitrile were purchased from Sigma-Aldrich.

Sucrose was purchased from NACALAI TESQUE, INC. As the primers, glucose, methyl glucoside (Me-GLC), and azidodeoxy glucoside ($N_3$-dGLC) were used. As the glucose, D-(+)-glucose was purchased from NACALAI TESQUE, INC. As the methyl glucoside, 1-methyl-α-D-glucopyranoside was purchased from NACALAI TESQUE, INC. As the azidodeoxy glucoside, 1-azido-1-deoxy-β-D-glucopyranoside was purchased from Sigma-Aldrich.

The other reagents were purchased from NACALAI TESQUE, INC. unless otherwise specified and guaranteed or higher-grade reagents were used.

Examples 1 to 5 and Comparative Example 1

The 200 mM phosphate buffer solution, the 1 M aqueous sucrose solution, the 1 M aqueous glucose solution, the SP solution, the CDP solution, and water were used and added to 5 mL-volume tubes such that the concentrations of the components became the concentrations described in Table 1 below to prepare 5 mL of reaction solutions. The pHs of the reaction solutions will be described in Table 1. The reaction solutions were sealed using Parafilms and incubated at 40° C. for 3 days. Subsequently, the tubes were heated at 100° C. for 5 minutes to inactivate the enzymes. The reaction solutions were transferred to 50 mL-volume centrifuge tubes, brought to a volume of 20 mL with water, centrifuged (15000 g) for 10 minutes, and subjected to removal of the supernatant to thereby perform purification. This purification procedure was repeated five times to obtain aqueous dispersions of a cellooligosaccharide. The obtained aqueous dispersions were dried at 70° C. for 24 hours to thereby provide dry products of the cellooligosaccharide and their yields were measured.

The obtained products are the cellooligosaccharide represented by the following Formula (4).

[Chem. 5]

(4)

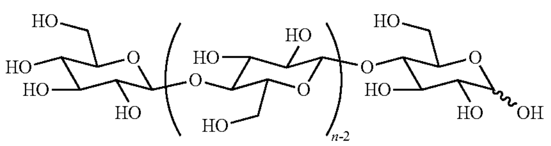

Examples 6 and 7

The same procedures as in Example 2 were performed except that, as the primer, the glucose was replaced by methyl glucoside (Me-GLC) in Example 6 and replaced by azidodeoxy glucoside ($N_3$-dGLC) in Example 7, to thereby obtain products and their yields were measured.

The obtained products are reducing-terminal-modified cellooligosaccharides represented by the following Formula (5) in Example 6 and the following Formula (6) in Example 7.

[Chem. 6]

(5)

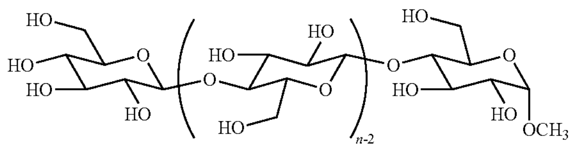

(6)

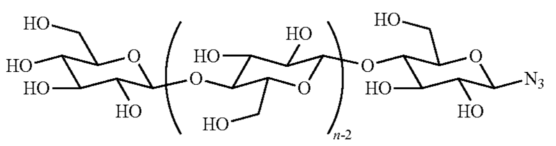

Example 8

The same procedures as in Example 2 were performed except that the incubation temperature in Example 2 was changed to 30° C., to thereby obtain a product and its yield was measured.

Example 9

The same procedures as in Example 2 were performed except that 0.25 mL of the water used for preparing the reaction solution in Example 2 was replaced by dimethyl sulfoxide (DMSO), so that the solvent of the reaction solution was changed to a mixed solvent containing 5 vol % of DMSO, to thereby obtain a product and its yield was measured.

Example 10

The same procedures as in Example 2 were performed except that 0.5 mL of the water used during preparation of the reaction solution in Example 2 was replaced by DMSO, so that the solvent of the reaction solution was changed to a mixed solvent containing 10 vol % of DMSO, to thereby obtain a product and its yield was measured.

Example 11

The same procedures as in Example 2 were performed except that 0.5 mL of the water used during preparation of the reaction solution in Example 2 was replaced by methanol, so that the solvent of the reaction solution was changed to a mixed solvent containing 10 vol % of methanol, to thereby obtain a product and its yield was measured.

Example 12

The same procedures as in Example 2 were performed except that 0.5 mL of the water used during preparation of the reaction solution in Example 2 was replaced by N,N-dimethylformamide (DMF), so that the solvent of the reaction solution was changed to a mixed solvent containing 10 vol % of DMF, to thereby obtain a product and its yield was measured.

Comparative Example 2

The 1 M HEPES buffer solution, the 1 M aqueous αG1P solution, the 1 M aqueous glucose solution, the CDP solution, and water were used and added to a 5 mL-volume tube such that the concentrations of the components respectively became 500 mM, 200 mM, 50 mM, and 0.2 U/mL; 5 mL of the prepared reaction solution was sealed using a Parafilm and incubated at 40° C. for 3 days. Subsequently, the tube was heated at 100° C. for 5 minutes to inactivate the enzyme. For the subsequent purification and drying steps, the same procedures as in Example 1 were performed to thereby obtain a product and the yield was measured.

The products obtained above were measured in terms of the average degree of polymerization (DP), the distribution of degrees of polymerization, and the percentage yield of such a cellooligosaccharide. The results will be described in Table 1. Note that the measurement methods are as follows.

(1) Average Degree of Polymerization

The average degree of polymerization of the cellooligosaccharide was measured by matrix assisted laser desorption/ionization time of flight mass spectrometry (MALDI-TOF-MS).

A standard sample used for calibration of mass-to-charge ratios was prepared in the following manner: 5 μL of an aqueous Bradykin fragment 1-7 solution (10 nmol/mL Bradykinin fragment 1-7, 0.05 mass % trifluoroacetic acid (TFA), and 50 mass % acetonitrile), 5 μL of an aqueous $P_{14}R$ solution (10 nmol/mL $P_{14}R$ and 0.1 mass % TFA), 5 μL of an aqueous ACTH fragment 18-39 solution (10 nmol/mL ACTH fragment 18-39 and 0.1 mass % TFA), 5 μL of a 10 mg/mL aqueous DHBA solution, 1 μL of an aqueous 1.0 mass % TFA solution, and 4 μL of acetonitrile were mixed together in a 1.7 mL tube.

The measurement sample of such a product was prepared by mixing together 1 μL of a 0.1% (w/v) aqueous dispersion of the product, 1 μL of a 10 mg/mL aqueous DHBA solution, and 3 μL of a trifluoroacetic acid (0.2 vol %) solution in acetonitrile in a Mighty vial having been rinsed with a solution of potassium hydroxide (3.3 mass %) in methanol.

Procedures of mounting and air-drying 1 μL of the standard sample and 1 μL of the measurement sample of the product on sample plates were repeated five times. The samples were dried in vacuum for 1 hour or more and measured by MALDI-TOF-MS (AXIMA-performance, SHIMADZU CORPORATION). The measurement conditions were Mode: Liner (positive), Mass Range: 1.0-3000.0, Max Leaser Rap Rate: 10, power: 100, profiles: 100, shots: 2, Ion Gate (Da): Blank500, and Pulsed Extraction optimized at (Da): 1000.0.

The MS spectrum obtained by the measurement was processed under conditions of Smoothing method: Gaussian, Smoothing filter width: 19, and Baseline filter width: 1000.

The measurement sample contains sodium ion adducts and potassium ion adducts and hence their peak areas were added, to determine the peak areas at the degrees of polymerization. From the ratios of the determined peak areas at the degrees of polymerization, the average of the degrees of polymerization was calculated as the average degree of polymerization.

(2) Distribution of Degrees of Polymerization

For the distribution of degrees of polymerization, the MALDI-TOF-MS spectrum obtained above was analyzed in accordance with the following formula, to thereby determine the standard deviation from the average degree of polymerization; and the standard deviation was defined as the distribution of degrees of polymerization.

[Math. 1]

$$\text{Standard deviation} = \sqrt{\frac{\sum\left(\text{Degrees of polymerization} - \text{Average degree of polymerization}\right)^2 \times \text{Peak areas at degrees of polymerization}}{\text{Sum of peak areas}}}$$

(3) Percentage Yield

For the percentage yield, from the yield and the average degree of polymerization of the cellooligosaccharide (product), the following formula was used to calculate the conversion ratio of the sucrose serving as the starting material.

[Math. 2

$$\text{Conversion ratio (\%)} = \frac{\text{Amount of substance of cellooligosaccharide (mol)} \times (\text{Average degree of polymerization of cellooligosaccharide} - 1)}{\text{Amount of substance of sucrose (mol)}} \times 100$$

TABLE 1

| | Example 1 | Example 2 | Example 3 | Example 4 | Example 5 | Example 6 | Example 7 | Example 8 |
|---|---|---|---|---|---|---|---|---|
| Phosphoric acid (mM) | 5 | 10 | 50 | 100 | 10 | 10 | 10 | 10 |
| Sucrose (mM) | 200 | 200 | 200 | 200 | 300 | 200 | 200 | 200 |
| Glucose (mM) | 50 | 50 | 50 | 50 | 50 | — | — | 50 |
| Me-GLC (mM) | — | — | — | — | — | 50 | — | — |
| $N_3$-dGLC (mM) | — | — | — | — | — | — | 50 | — |
| SP (U/mL) | 0.2 | 0.2 | 0.2 | 0.2 | 0.2 | 0.2 | 0.2 | 0.2 |
| CDP (U/mL) | 0.2 | 0.2 | 0.2 | 0.2 | 0.2 | 0.2 | 0.2 | 0.2 |
| αG1P (mM) | — | — | — | — | — | — | — | — |
| Solvent of reaction solution | Water | Water | Water | Water | Water | Water | Water | Water |
| Reaction temperature (° C.) | 40 | 40 | 40 | 40 | 40 | 40 | 40 | 30 |
| pH of reaction solution | 7.4 | 7.4 | 7.4 | 7.4 | 7.4 | 7.4 | 7.4 | 7.4 |
| Percentage yield (%) | 58 | 83 | 81 | 59 | 79 | 84 | 81 | 59 |
| Average degree of polymerization | 8.1 | 8.2 | 8.2 | 8.2 | 9.0 | 8.1 | 8.2 | 8.2 |
| Distribution of degrees of polymerization | 1.30 | 1.24 | 1.25 | 1.32 | 1.30 | 1.23 | 1.25 | 1.23 |

| | Example 9 | Example 10 | Example 11 | Example 12 | Comparative Example 1 | Comparative Example 2 |
|---|---|---|---|---|---|---|
| Phosphoric acid (mM) | 10 | 10 | 10 | 10 | 150 | — |
| Sucrose (mM) | 200 | 200 | 200 | 200 | 200 | — |
| Glucose (mM) | 50 | 50 | 50 | 50 | 50 | 50 |
| Me-GLC (mM) | — | — | — | — | — | — |
| $N_3$-dGLC (mM) | — | — | — | — | — | — |
| SP (U/mL) | 0.2 | 0.2 | 0.2 | 0.2 | 0.2 | — |
| CDP (U/mL) | 0.2 | 0.2 | 0.2 | 0.2 | 0.2 | 0.2 |
| αG1P (mM) | — | — | — | — | — | 200 |
| Solvent of reaction solution | DMSO 5% | DMSO 10% | MeOH 10% | DMF 10% | Water | Water |
| Reaction temperature (° C.) | 40 | 40 | 40 | 40 | 40 | 40 |
| pH of reaction solution | 7.4 | 7.4 | 7.4 | 7.4 | 7.4 | 7.5 |
| Percentage yield (%) | 76 | 73 | 78 | 76 | 38 | 35 |
| Average degree of polymerization | 8.0 | 7.8 | 8.0 | 7.7 | 8.1 | 8.1 |
| Distribution of degrees of polymerization | 1.07 | 0.88 | 0.90 | 0.85 | 1.43 | 1.17 |

The obtained products were subjected to infrared spectroscopy (IR) and demonstrated to have cellulose II crystalline structures. In Examples 1 to 12, the two-stage synthesis provided cellooligosaccharides similar to the cellooligosaccharide in Comparative Example 2 provided by the one-stage synthesis and there were also not considerable differences in average degree of polymerization.

On the other hand, in Examples 1 to 12, compared with the one-stage synthesis of Comparative Example 2, the cellooligosaccharides had greatly increased percentage yields. In particular, comparison between Examples 1 to 4 revealed that, in the cases of concentrations of phosphoric acid of 10 mM and 50 mM, the percentage yields were markedly high. By contrast, in Comparative Example 1 in which the concentration of phosphoric acid was more than 120 mM, the percentage yield was low and the percentage yield was as low as that in the one-stage synthesis of Comparative Example 2.

Example 6, which used, as the primer, methyl glucoside, was subjected to MALDI-TOF-MS and demonstrated that a cellooligosaccharide having a reducing terminal substituted with a methoxy group was generated. In other words, the reducing-terminal-modified cellooligosaccharide was also generated by the two-stage synthesis. In addition, Table 1 demonstrates that such a reducing-terminal-modified cellooligosaccharide is generated at a percentage yield and a distribution of degrees of polymerization that are similar to those of unmodified cellooligosaccharides.

Example 7, which used, as the primer, azidodeoxy glucoside, was subjected to proton nuclear magnetic resonance ($^1$H-NMR) measurement and demonstrated that the peak derived from the reducing terminal disappeared, compared with unmodified cellooligosaccharides. In addition, Fourier transform infrared spectroscopy (FT-IR) demonstrated the presence of a peak at or about 2120 $cm^{-1}$ derived from an azide group. This demonstrated that the reducing terminal was modified with an azide group. Table 1 demonstrates that such an azide adduct cellooligosaccharide is generated at a percentage yield and a distribution of degrees of polymerization that are similar to those of unmodified cellooligosaccharides.

The $^1$H-NMR and FT-IR measurements were performed for freeze-dried products. For $^1$H-NMR, AV-400M manufactured by Bruker Corporation was used; about 15 mg of a cellooligosaccharide was dissolved in 500 μL of 4% sodium deuteroxide solution in deuterium oxide and measured under a condition of 16 scans. For FT-IR, Nicolet6700 manufactured by Thermo Scientific was used under conditions of the ATR method, a resolution of 2 $cm^{-1}$, and 32 scans.

Examples 9 to 11 are examples using a mixed solvent containing water and a water-soluble organic solvent in which the mixed solvent was used in a reaction system of a two-stage synthesis, to thereby provide a smaller distribution of degrees of polymerization than in Example 2.

Some embodiments according to the present invention have been described so far; however, these embodiments are provided as examples and are not intended to limit the scope of the invention. These embodiments can also be carried out in various other forms and various omissions, replacements, and changes can be performed without departing from the spirit and scope of the invention. These embodiments and their omissions, replacements, changes, and the like are included in the scope and spirit of the invention and similarly included in the invention described in Claims and the range of equivalents.

The invention claimed is:

1. A method for producing a cellooligosaccharide, the method comprising a reaction step of subjecting (i) at least one primer selected from the group consisting of glucose and cellobiose and (ii) sucrose, in the presence of phosphoric acid, to actions of sucrose phosphorylase from *Leuconostoc mesenteroides* and cellodextrin phosphorylase from *Clostridium thermocellum*, wherein, in a reaction system, a concentration of phosphoric acid including an amount of a-glucose-1-phosphate contained as an intermediate product is 3 $mol/m^3$ or more and 120 $mol/m^3$ or less.

2. The method for producing a cellooligosaccharide according to claim 1, wherein a reaction temperature is 25° C. or more and 45° C. or less.

3. The method for producing a cellooligosaccharide according to claim 1, wherein, in a mixed solvent including water and a water-soluble organic solvent, the primer and the sucrose are subjected to actions of the sucrose phosphorylase and the cellodextrin phosphorylase.

4. The method for producing a cellooligosaccharide according to claim 1, wherein the primer is glucose.

5. The method for producing a cellooligosaccharide according to claim 2, wherein, in a mixed solvent including water and a water-soluble organic solvent, the primer and the sucrose are subjected to actions of the sucrose phosphorylase and the cellodextrin phosphorylase.

6. The method for producing a cellooligosaccharide according to claim 2, wherein the primer is glucose.

* * * * *